US006776963B1

(12) United States Patent
Akporiaye et al.

(10) Patent No.: US 6,776,963 B1
(45) Date of Patent: Aug. 17, 2004

(54) MULTIPLE PARALLEL CATALYTIC REACTOR ASSEMBLY

(75) Inventors: Duncan E. Akporiaye, Oslo (NO); Arne Karlsson, Oslo (NO); Ivar M. Dahl, Oslo (NO); Rune Wendelbo, Oslo (NO)

(73) Assignee: UOP LLC, Des Plaines, IL (US)

(*) Notice: Subject to any disclaimer, the term of this patent is extended or adjusted under 35 U.S.C. 154(b) by 930 days.

(21) Appl. No.: 09/611,071

(22) Filed: Jul. 6, 2000

Related U.S. Application Data (63) Continuation-in-part of application No. 09/465,213, filed on Dec. 15, 1999, now Pat. No. 6,576,196.

(51) Int. Cl.[7] .............................................. G01N 31/10
(52) U.S. Cl. ..................... 422/82.12; 422/99; 422/101; 422/102; 422/103; 422/104; 422/130; 436/37
(58) Field of Search ................................ 422/82.12, 99, 422/101–104, 130, 239, 139–141, 145–146; 436/155, 159, 161, 173, 34, 37

(56) References Cited

U.S. PATENT DOCUMENTS

| 4,014,657 A | 3/1977 | Gryaznov et al. ......... 23/288 R |
| 5,112,574 A | 5/1992 | Horton ....................... 422/102 |
| 5,304,354 A | 4/1994 | Finley et al. ............... 422/196 |

(List continued on next page.)

FOREIGN PATENT DOCUMENTS

| DE | 198 09 477 A1 | 9/1999 |
| WO | WO96/11878 A1 | 4/1996 |
| WO | WO97/30784 A1 | 8/1997 |
| WO | WO97/32208 A1 | 9/1997 |
| WO | WO98/07026 A1 | 2/1998 |
| WO | WO98/36826 A1 | 8/1998 |
| WO | WO98/39099 | 9/1998 |
| WO | WO 98/52685 | 11/1998 |
| WO | WO99/19724 A1 | 4/1999 |
| WO | WO99/34206 A1 | 7/1999 |
| WO | WO99/64160 | 12/1999 |
| WO | WO00/09255 | 2/2000 |

OTHER PUBLICATIONS

Font et al.; Ind. Eng. Chem. Prod. Res. Dev., 1986 (25); pp. 491–496.*
Senekan; Nature, Jul. 1998, 394 (23); pp. 350–353.*
Akporiaye, D. E.; Dahl, I. M.; Karlsson, A.; Wendelbo, R. Angew Chem. Int. Ed. 1998, 37, 609–611.
Holzwarth, A.; Schmidt, H.; Maier, W. F. Angew. Chem. Int. Ed., 1998, 37, 2644–2647.
Bein, T. Angew. Chem. Int. Ed., 1999, 38, 323–326.
Taylor, S. J.; Morken, J. P. Science, Apr. 1998, 280(10), 267–270.
Cong, P.; Doolen, R. D.; Fan, Q.; Giaquinta, D. M.; Guan, S.; McFarland, E. W.; Poojary, D. M.; Self, K.; Turner, H. W.; Weinberg, W. H. Angew Chem. Int. Ed. 1999, 38, 484–488.
Klien, J.; Lehmann, C. W.; Schmidt, H.; Maier, W. F. Angew Chem,. Int. Ed. 1998, 37, 3369–3372.

*Primary Examiner*—Jerry D. Johnson
*Assistant Examiner*—Basia Ridley
(74) *Attorney, Agent, or Firm*—John G. Tolomei; Frank S. Molinaro; Maryann Maas (57) ABSTRACT

A multiple parallel catalytic reactor assembly has been developed. The assembly has (1) a plurality of vessels for containing catalyst, each vessel having an open end and a fluid permeable end; (2) a plurality of bottoms, each bottom having an open end and a closed end with the plurality being supported by a single first support plurality of vessels positioned within the plurality of bottoms; (3) a plurality of tops supported by a single second support with the plurality of tops engaged with the plurality of bottoms to form a plurality of sealed independent reaction chambers; (4) a plurality of first fluid conduits in fluid communication with the reaction chambers; (5) a plurality of second fluid conduits in fluid communication with the reaction chambers; and (6) a plurality of microporous structures in alignment with the open ends of said vessels.

24 Claims, 4 Drawing Sheets

U.S. PATENT DOCUMENTS

| | | | |
|---|---|---|---|
| 5,405,586 A | 4/1995 | Koves | 422/218 |
| 5,489,726 A | 2/1996 | Huss, Jr. et al. | 585/671 |
| 5,609,826 A | 3/1997 | Cargill et al. | 422/99 |
| 5,612,002 A | 3/1997 | Cody et al. | 422/131 |
| 5,746,982 A | 5/1998 | Saneii et al. | 422/134 |
| 5,766,556 A | 6/1998 | DeWitt et al. | 422/131 |
| 5,785,927 A | 7/1998 | Scott et al. | 422/104 |
| 5,792,431 A | 8/1998 | Moore et al. | 422/134 |
| 6,030,917 A | 2/2000 | Weinberg et al. | 502/104 |
| 6,045,671 A | 4/2000 | Wu et al. | 204/298.11 |
| 6,056,926 A | 5/2000 | Sugarman et al. | 422/131 |

* cited by examiner

MULTIPLE PARALLEL CATALYTIC REACTOR ASSEMBLY

CROSS REFERENCE TO RELATED APPLICATION

The present application is a continuation-in-part of related application U.S. application Ser. No. 09/465,213 filed Dec. 15, 1999, now U.S. Pat. No. 6,576,196 which is hereby incorporated by reference in its entirety.

FIELD OF THE INVENTION

The present invention relates to a multiple parallel catalytic reactor assembly.

BACKGROUND OF THE INVENTION

Before a catalyst is selected for use in a commercial application, a great number of known catalysts may be contemplated for use in the envisioned application. A large number of newly synthesized catalytic compositions may also be considered as candidates. It then becomes important to evaluate each of the potential catalysts to determine the formulations that are the most successful in catalyzing the reaction of interest under a given set of reaction conditions.

Two key characteristics of a catalyst that are determinative of its success are the activity of that catalyst and the selectivity of the catalyst. The term "activity" refers to the rate of conversion of reactants by a given amount of catalyst under specified conditions, and the term "selectivity" refers to the degree to which a given catalyst favors one reaction compared with another possible reaction; see *McGraw-Hill Concise Encyclopedia of Science and Technology*, Parker, S. B., Ed. in Chief; McGraw-Hill: N.Y., 1984; p. 854.

The traditional approach to evaluating the activity and selectivity of new catalysts is a sequential one. When using a micro-reactor or pilot plant, each catalyst is independently tested at a set of specified conditions. Upon completion of the test at each of the set of specified conditions, the current catalyst is removed from the micro-reactor or pilot plant and the next catalyst is loaded. The testing is repeated on the freshly loaded catalyst. The process is repeated sequentially for each of the catalyst formulations. Overall, the process of testing all new catalyst formulations is a lengthy process at best.

Developments in combinatorial chemistry have first largely concentrated on the synthesis of chemical compounds. For example, U.S. Pat. No. 5,812,002 and U.S. Pat. No. 5,766,556 disclose a method and apparatus for multiple simultaneous synthesis of compounds. WO 97/30784-A1 discloses a microreactor for the synthesis of chemical compounds. Akporiaye, D. E.; Dahl, I. M.; Karlsson, A.; Wendelbo, R. *Angew Chem. Int. Ed.* 1998, 37, 609–611 disclose a combinatorial approach to the hydrothermal synthesis of zeolites; see also WO 98/36826. Other examples include U.S. Pat. Nos. 5,609,826, 5,792,431, 5,746,982, 5,785,927, and WO 96/11878-A1.

Combinatorial approaches have been applied to catalyst testing to expedite the testing process. For example, WO 97/32208-A1 teaches placing different catalysts in a multi-cell holder. The reaction occurring in each cell of the holder is measured to determine the activity of the catalysts by observing the heat liberated or absorbed by the respective formulation during the course of the reaction, and/or analyzing the products or reactants. Thermal imaging has been used as part of other combinatorial approaches to catalyst testing; see Holzwarth, A.; Schmidt, H.; Maier, W. F. *Angew. Chem. Int. Ed.*, 1998, 37, 2644–2647, and Bein, T. *Angew. Chem. Int. Ed.*, 1999, 38, 323–326. Thermal imaging may be a tool to learn some semi-quantitative information regarding the activity of the catalyst but it provides no indication as to the selectivity of the catalyst.

Some attempts to acquire information as to the reaction products in rapid-throughput catalyst testing are described in Senkam, S. M. *Nature*, July 1998, 384(23), 350–353, where laser-induced resonance-enhanced multiphoton ionization is used to analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Tuner, H. W.; Weinberg, W. H. *Angew Chem. Int. Ed.* 1999, 38, 484–488 teaches using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

More recently combinatorial chemistry has been applied to evaluate the activity of catalysts. Some applications have focused on determining the relative activity of catalysts in a library; see Klien, J.; Lehmann, C. W.; Schmidt, H.; Maler, W. F. *Angew Chem. Int. Ed.* 1998, 37, 3369–3372; Taylor, S. J.; Morken, J. P. *Science*, April 1998, 280(10), 267–270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons which are detected by microelectrode collection. WO 98/07026-A1 discloses miniaturized reactors where the reaction mixture is analyzed during the reaction time using spectroscopic analysis. Some commercial processes have operated using multiple parallel reactors where the products of all of the reactors are combined into a single product stream; see U.S. Pat. No. 5,304,354 and U.S. Pat. No. 5,489,726. U.S. Pat. No. 5,112,574 discloses an array of stoppers that may be inserted into the wells of any multititer plate.

A multiple parallel reactor assembly to simultaneously test a plurality of catalysts in a rapid, economical, and consistent way has been developed. The invention allows for easy simultaneous assembly of the multiple parallel reactors. The tops and bottoms forming the multiple parallel reaction chambers are attached to supports, one support for the plurality of tops and another support for the plurality of bottoms, so that assembly involves manipulating only the two supports instead of individually manipulating the significantly larger number of individual components. However, the present invention retains a great deal of flexibility by not fully integrating the key components into the supports. Each key component is individually removable from the support. Worn or defective components are readily individually replaced without disturbance to other components. Similarly, the vessels containing the catalyst particles are housed within the bottoms can be individually removed. The number of parallel reactors in the assembly is readily varied through the addition or subtraction of as little as one set of key components.

SUMMARY OF THE INVENTION

The purpose of the invention is to provide a multiple parallel catalytic reactor assembly having (1) a plurality of bottoms, each bottom having an open end and a closed end with the plurality being supported by a single first support; (2) a plurality of tops supported by a single second support with the plurality of tops engaged with the plurality of vessels to form a plurality of sealed independent reaction chambers; (3) a plurality of vessels for containing catalyst, each vessel having an open end and a fluid permeable end, and positioned within the reaction chambers so that the open ends of the vessels are in alignment with the open ends of the bottoms (4) a plurality of first fluid conduits in fluid communication with the reaction chambers, and (5) a plurality of second fluid conduits in fluid communication with the reaction chambers. A specific embodiment of the invention is one where one or more heaters are positioned adjacent the plurality of bottoms to heat the bottoms and the reaction chambers. Another specific embodiment of the invention is one where one or more seals are used to engage the plurality of bottoms and the corresponding plurality of tops and optionally another seal or seals are used to engage the plurality of vessels and the plurality of tops to form the sealed reaction chambers.

Another purpose of the invention is to provide a process for conducting multiple parallel catalyst evaluations using the multiple parallel catalytic reactor assembly described above with the advantage of simultaneously sealing all of the open ends of the plurality of bottoms with the plurality of corresponding tops to form the multiple sealed independent reaction chambers. A specific embodiment of the invention also includes simultaneously opening all the multiple sealed reaction chambers by removing the plurality of tops from the open ends of the plurality of bottoms. Another specific embodiment of the invention is one where the plurality of vessels containing catalyst are removed from the plurality of bottoms.

DETAILED DESCRIPTION OF THE INVENTION

In general terms, the present invention is a multiple parallel catalytic reactor assembly where each reactor in the assembly has several key components. Each reactor has a bottom having an open end and a closed end and each reactor also has a top which engages the open end of the bottom to form a sealed reaction chamber. Within the sealed reaction chamber, each reactor has a vessel having an open end and a fluid permeable end and contains catalyst. Finally, the sealed reaction chamber of each reactor is in fluid communication with two fluid conduits. Two or more individual reactors may be used in the assembly. The assembly is also quite flexible, allowing the number of individual reactors in the assembly to be adjusted with ease.

As mentioned above, each reactor in the parallel catalytic reactor assembly contains a bottom that has a closed end and an open end. Note, however, that the closed end may contain a fluid conduit as discussed below. The bottoms are constructed of materials selected to withstand the temperatures, pressures and chemical compounds of the particular application. Examples of suitable materials include metals and their alloys, low grade steel, and stainless steels, superalloys like incollsy, inconel, hastalloy, engineering plastics and high temperature plastics, ceramics such as silicon carbide and silicon nitride, glass, quartz, Teflon polymer, nylon, low temperature plastics such as polyethylene, polypropylene, and polyetherether ketone. It is not necessary that each vessel in the plurality be constructed of the same material.

The bottom is preferably cylindrical in shape, but may be of other geometric shapes. For example, the cross-section of the bottom may be in the shape of a square, an ellipse, a rectangle, a polygon, "D"-shaped, segment- or pie-shaped, a chard, a cone or the like. For ease of discussion, the bottom is discussed here as having a cylindrical shape. The bottom has a top end, sides, and a bottom end. The top end is open and the bottom end is permanently closed. The preferred volume of the bottoms ranges from about 0.001 $cm^3$ to about 10 $cm^3$ with two most preferred volumes being 0.1 $cm^3$ and 1 $cm^3$. The preferred size of the bottoms ranges from a length/diameter ratio of about 1 to about 20. It is more preferred that the length/diameter of the bottoms be greater than 4 and ideally 5 or 10. It is preferred that the bottoms be constructed of material that is able to withstand temperatures of from about 10° C. to about 1000° C. It is contemplated that the equipment may be used in applications that require cooling, and therefore in some specific applications the bottoms should be constructed of material that is able to withstand temperatures as low as −70° C. It is also preferred that the bottoms be constructed of material having good heat transfer properties and that the material of construction is inert in the reaction being conducted. While it may be preferred, all the bottoms in the plurality are not necessarily identical. The geometry, size, volume, and material of construction may be varied between bottoms within the plurality.

Each of the bottoms is a freestanding unit or independent piece of apparatus, however, significant advantages are achieved through attaching each of the bottoms to a single support. The attachment of all of the bottoms to a single support operates to provide the benefits of having all of the bottoms maneuverable as a single unit, while maintaining the flexibility of replacing any or all of the individual bottoms as necessary. For example, it is far more convenient for handling and assembly to be able to manipulate a single support as opposed to individually manipulating multiple bottoms. Also, robotics, which are frequently used in combinatorial application, are more readily adapted to manipulating a single tray. Furthermore, as will be discussed in greater detail below, the assembly of the reactors is reduced to a single step which simultaneously seals and forms the multiple parallel reactors. Although less preferred, two-stage action is within the scope of the present invention. The attachment may be fixed, or may be temporary such as using bolts or fasteners.

The support may provide for the attachment of any number of individual bottoms. For example, a support may attach 6, 8, 12, 24, 48, 96, and 384 bottoms. Ease of handling is only one of the benefits of the support, flexibility is another. In any given application, the full capacity of a support need not be utilized, i.e., a support capable of supporting 24 bottoms may be used to support only two bottoms. The system is very flexible in that the number of bottoms in use is easily altered by simply adding or removing bottoms to the support. Similarly, should one bottom of a plurality become worn or damaged, that single bottom may be independently replaced without replacement of other bottoms in the plurality.

As with the bottom itself, the support may be constructed of a variety of materials including metals and their alloys, low grade steel, and stainless steels, super-alloys like incollsy, inconel, hastalloy, engineering plastics and high temperature plastics, ceramics such as silicon carbide and silicon nitride, glass, quartz, Teflon polymer, nylon, and low temperature plastics such as polyethylene, polypropylene, and polyetherether ketone. The support may allow for the attachment of the vessels in any number of geometrical patterns with the preferred being a grid. It is preferred that the support have dimensions similar to the dimensions of commonly used microtiter trays. It is preferred that the support be constructed of material that is able to withstand temperatures of from about 10° C. to about 1000° C., and for many catalytic reactions, the support may be required to withstand temperatures ranging from about 300° C. to about 1000° C. As discussed above, in some applications requiring cooling, the support may be constructed of material able to withstand temperatures as low as −70° C.

The multiple parallel catalytic reactor assembly of the present invention may optionally contain one or more heaters to heat at least a portion of one or more of the bottoms. For many reactions, the catalyst used in the reaction must be heated to a desired temperature range. The multiplicity of bottoms may be heated as a unit or each bottom may be individually heated. All heated bottoms may be heated to the same temperature, or different individual bottoms may be heated to different temperatures. The portion of the bottom that is heated is usually that portion closest to the location of the catalyst (discussed below), and generally, it is preferred that the closed end of the bottoms be heated.

The multiple parallel catalytic reactors of the present invention further contain a plurality of tops which correspond to the plurality of bottoms. The tops engage the open ends of the bottoms to form sealed reaction chambers. Therefore, for every bottom in the plurality there must be a corresponding top. Like the bottoms, the tops may be constructed of a variety of materials including metals and their alloys, low grade steel, and stainless steels, super-alloys such as incollsy, inconel, hastalloy, engineering plastics and high temperature plastics, ceramics such as silicon carbide and silicon nitride, glass, quartz, Teflon polymer, nylon, and low temperature plastics such as polyethylene, polypropylene, and polyetherether ketone. The support for the tops may be required to withstand temperatures from 10° C. to about 1000° C., but a preferred range of temperatures includes temperatures ranging from about 10° C. to about 350° C. It is also contemplated that in some applications, the support for the tops may be required to withstand temperatures as low as −70° C. It is preferred that each top in the plurality be constructed of the identical material, but it is not necessary. Similarly, in some applications it may be preferred that the plurality of tops be constructed of the same material as the corresponding plurality of bottoms, but again it is not necessary. For example, in the situation where only the closed end of the bottoms are heated, heat resistant material may be used for the construction of the bottoms, where non-heat resistant material may be used for the corresponding tops. It is preferred that the length of the bottoms be sufficient so that the tops are not affected by the heater used at the closed end of the bottoms, thereby allowing lower temperature materials to be used for the construction of the tops.

It is preferred that the overall shape of the tops conform to the shape of the corresponding bottoms so that the tops may adequately engage the bottoms to form sealed reaction chambers. The tops may be formed so as to merely seal the open end of the bottoms, or the top may extend within the open end of the bottoms to further define the reaction chambers. If necessary, one or more seals may be used to engage both the bottoms and the tops to form the sealed reaction chambers. One seal may be used to engage both the plurality of bottoms and the plurality of tops, or each set of a bottom and its corresponding top may have an independent seal. As discussed below, the seal(s) may also seal the vessel. An advantage of the present invention is that seals that function only at lower temperatures may be employed even if the catalyst in the reaction chamber is to be heated to a high temperature. In such a situation, the catalyst is contained near the closed end of the bottoms and only the closed end of the bottoms are heated. The lengths of the bottoms are preferably chosen so that the position of the seal(s) is a sufficient distance from the heater and the seal(s) is not affected by the heat. It is most preferred that the seals be prevented from exceeding 200° C.

As with the bottoms, each of the tops is a freestanding unit or independent piece of apparatus. Again, however, significant advantages are achieved by attaching each of the tops to a single support. Manual or robotic handling and assembly is simplified by manipulating a single support as opposed to individually manipulating multiple bottoms. Furthermore, as will be discussed in greater detail below, the assembly of the reactors is reduced to a single step which simultaneously seals and forms the multiple parallel reactors.

The support for the tops may provide for the attachment of any number of individual tops. For example, a support may attach 6, 8, 12, 24, 48, 96, 384, and 1264 tops. As with the bottoms, ease of handling is only one of the benefits of the support, and flexibility is another. In any given application, the full capacity of a support need not be utilized, i.e., a support capable of supporting 24 tops may be used to support only two tops. The system is very flexible in that the number of tops in use is easily altered by simply adding or removing one or more tops to the support. Similarly, should a top of a plurality become worn or damaged, that single top may be independently replaced without replacement of other tops in the plurality.

As with the tops themselves, the support for the tops may be constructed of a variety of materials including metals and their alloys, low grade steel, and stainless steels, super-alloys like incollsy, inconel, hastalloy, engineering plastics and high temperature plastics, ceramics such as silicon carbide and silicon nitride, glass, quartz, Teflon polymer, nylon, and low temperature plastics such as polyethylene, polypropylene, and polyetherether ketone. The support for the tops may be required to withstand temperatures from 10° C. to about 1000° C., but a preferred range of temperatures includes temperatures ranging from about 10° C. to about 350° C. In some applications, it is anticipated that the support for the tops may be required to withstand temperatures as low as −70° C. The support may allow for the attachment of the tops in any number of geometrical patterns with the preferred support being a grid arrangement. However, it is important that the arrangement of the tops be such that it allows for each top to properly engage its corresponding bottom to form the sealed reaction chambers. It is therefore preferred that the arrangement of the tops coordinate with the arrangement of the bottoms.

Another component of the present invention is a plurality of vessels to contain the catalyst. Each vessel has an open end and a fluid permeable end. Catalyst is added to the vessels through the open end. The same catalyst may be placed in all of the vessels or each individual vessel may contain a different catalyst or mixtures of different catalysts. The same mixture of two or more catalysts may be in each individual vessel, but each at different relative component ratios. The vessel is positioned within the sealed reaction chamber formed by the tops and the bottoms. The open ends of the vessels are in alignment with, or adjacent to, the open ends of the bottoms and the fluid permeable ends of the vessels are oriented to be adjacent the closed ends of the bottoms. The vessel may be supported within the bottom by one or more supports. One or more seals may be used to engage both the vessels and the corresponding tops to form a catalyst zone. Seals aid in containing the catalyst within the vessels and directing the fluid flow in the proper path for the application. Again, when a heater is employed, it is preferred that the bottoms and vessels be sized so that the seals engaging the tops and the vessels be a sufficient distance from the heater so that the seals do not exceed their useful temperature. It is most preferred that the seals be prevented from exceeding 200° C.

The vessels may be in any of the shapes described above for the bottoms and may be constructed of any of the materials described above for the bottoms or the tops. It is preferred that the vessels be of the same overall shape as the bottoms and constructed of the same material as the bottoms. The fluid permeable end contains a microporous containment device which may be constructed of any material that is capable of retaining solid particles while allowing gas or liquid to pass through. The microporous containment device is attached at or near the fluid permeable end of the vessel and extends across the cross-section, or internal diameter, of the vessel. Examples include frits, membranes, or fine meshed screens. Suitable frits include sintered metal, glass, sintered glass, and raney metals. Suitable membranes include electro-bonded films and etched alloy films. Frits are preferred for the microporous containment device, and it is preferred that the frit cover as much of the cross-section of vessel as possible, and most preferred that the frit cover as close to 100 percent of the cross-section of the vessel as practical. It is most preferred to have a frit with small passages so that the fluid is well dispersed after passing through the frit. The interior volume of space defined by the top, the sides of the vessel, and the microporous containment device at the fluid permeable end of the vessel is a catalyst zone and contains the solid catalyst particles.

As in most catalytic reactions, it is necessary to add at least one reactant to contact the catalyst and to form a reaction mixture. Effluent is then withdrawn, typically for analysis. Therefore, each of the multiple reaction chambers of the present invention is in fluid communication with at least two fluid conduits, one to allow the addition of fluid reactant and the other to allow for the withdrawal of the resulting effluent. Both fluid conduits may be connected to the tops or the support for the tops and in fluid communication with the reaction chambers, or both fluid conduits may be connected to the bottoms or the support for the bottoms and in fluid communication with the reaction chambers. Alternately, one fluid conduit may be connected to the tops or the support for the tops and in fluid communication with the reaction chambers, while the other fluid conduit may be connected to the bottoms or the support for the bottoms and in fluid communication with the reaction chambers. In some particular applications it may be preferred that both fluid conduits be connected to the tops or the support for the tops. The fluid conduits may be fixed in their connections, or may be easily disconnected through the use of seals.

One benefit to having both fluid conduits connected to the tops or the support for the tops is the simplification of the overall assembly of the apparatus, thus the ease of use of the apparatus. As discussed below, assembling the key components may be simplified when the fluid conduits are all positioned on the same side of the apparatus. Furthermore, placement of the apparatus of the invention into other devices may be simplified by having all of the fluid conduits on the same side of the apparatus. For example, placing the closed ends of the bottoms of the assembled apparatus into a heater is simplified when all of the conduits are located on the same side of the apparatus.

The fluid conduits for the inlet of the reactant are positioned so that the fluid flow of the reactant enters the reaction chambers and passes through the fluid permeable end of the vessel to enter the catalyst zone and contact the catalyst. The fluid conduits for the withdrawal of the effluents are positioned so that the effluents are withdrawn from the catalyst zones without disrupting the flow of reactants. The seals also help to control the fluid flow in the proper direction.

The fluid conduits may further contain a structure to prevent solid catalyst particles from being removed with the fluid effluent such as a microporous containment device, which may be constructed of any material that is capable of retaining solid particles while allowing gas or liquid to pass through. The microporous containment device may be attached to the fluid conduit near the vessel and extend across the cross-section, or internal diameter, of the fluid conduit. Examples of microporous containment devices include frits, membranes, or fine meshed screens. Suitable frits include sintered metal, glass, sintered glass, and raney metals. Suitable membranes include electro-bonded films and etched alloy films. Frits are preferred for the microporous containment device, and it is preferred that the frit cover as much of the cross-section of fluid conduit as possible and most preferred that the frit cover as close to 100 percent of the cross-section of the fluid conduit as practical.

Alternatively, the microporous containment device may be attached in a manner so that it protrudes into the vessel and extends at least partially across the cross-section, or internal diameter, of the vessel. The microporous containment device may be attached to the fluid conduit, to the top, or to the vessel. Again, the purpose of the microporous containment device is to retain solid particles within the vessel and prevent the solid particles from being removed from the vessel with the fluid effluent.

In heterogeneous catalytic applications, it is necessary to be able to open reactors in order to add or remove solid catalyst particles within the vessels. Note that the catalyst particles may be removed, or, for added convenience, it may be preferred that the entire vessel containing the catalyst be removed and replaced with another vessel containing another catalyst to be evaluated. The multiple parallel catalytic reactor assembly of the present invention provides a significant advantage in that the assembly may be opened and closed with ease. With all of the bottoms attached to a single support and all of the tops also attached to a single top support, the two halves may be readily closed in a single step to form the multiple sealed reaction chambers. It is not necessary to close each reactor individually, sequentially, one by one. All reactors are closed simultaneously by placing the top support containing all of the tops in alignment over the corresponding bottom support containing all of the bottoms. While the reactors are closed and sealed, the fluid conduits in fluid communication with the reaction chambers provide the conduits for the introduction of reactant into the reaction chambers and the withdrawal of effluent from the reaction chambers without opening the reactors. Repeated opening and closing of the reactors to introduce reactants and remove products are not necessary. The reactor may remain closed until solid catalyst particles need to be added or removed. When the reactors need to be opened to add or remove solid catalyst particles, all of the reactors are opened simultaneously in a single step by removing the top support containing all of the tops from vertical alignment over the corresponding bottom support containing all of the bottoms.

The fit of the tops into the open end of the bottoms may provide enough of a seal to maintain the sealed reaction chambers. However, if necessary, the tops may be held in place over the bottoms by a locking device. Numerous locking devices are known in the art for holding two supports together. For example, clamps, bolts, frames, and springs are all known locking devices that may be successfully employed in the present invention.

An optional component in the present invention is a plurality of thermocouples. The plurality of thermocouples extends into the reaction chamber in order to measure the temperature of the solid catalyst particles. It is preferred that the thermocouples extend through the fluid conduit that is in more direct fluid communication with the catalyst zone and into the catalyst zone.

Figure 1:
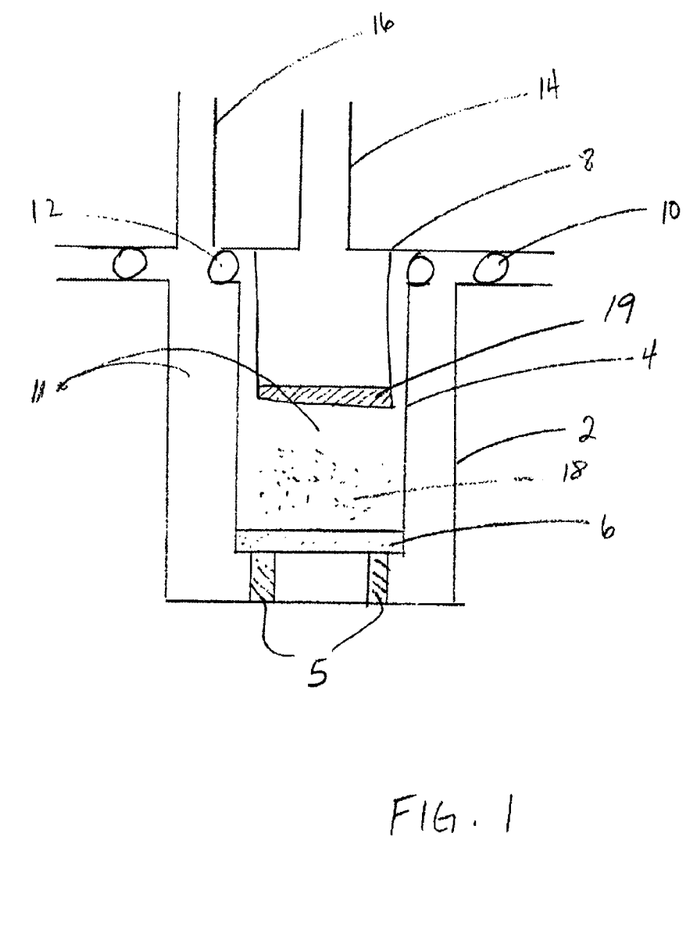
FIG. 1 is a side view of one specific embodiment of a single reactor of the multiple parallel catalytic reactor assembly of the present invention.
Figure 2:
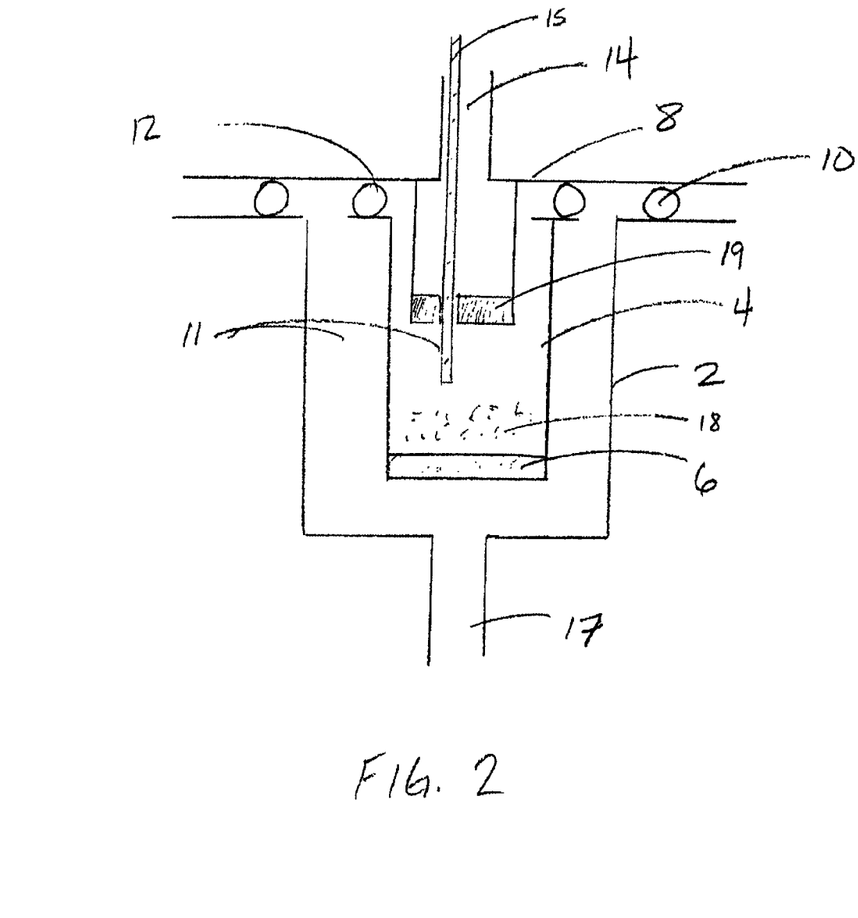
FIG. 2 is a side view of another specific embodiment of a single reactor of the multiple parallel catalytic reactor assembly of the present invention.
Figure 3:
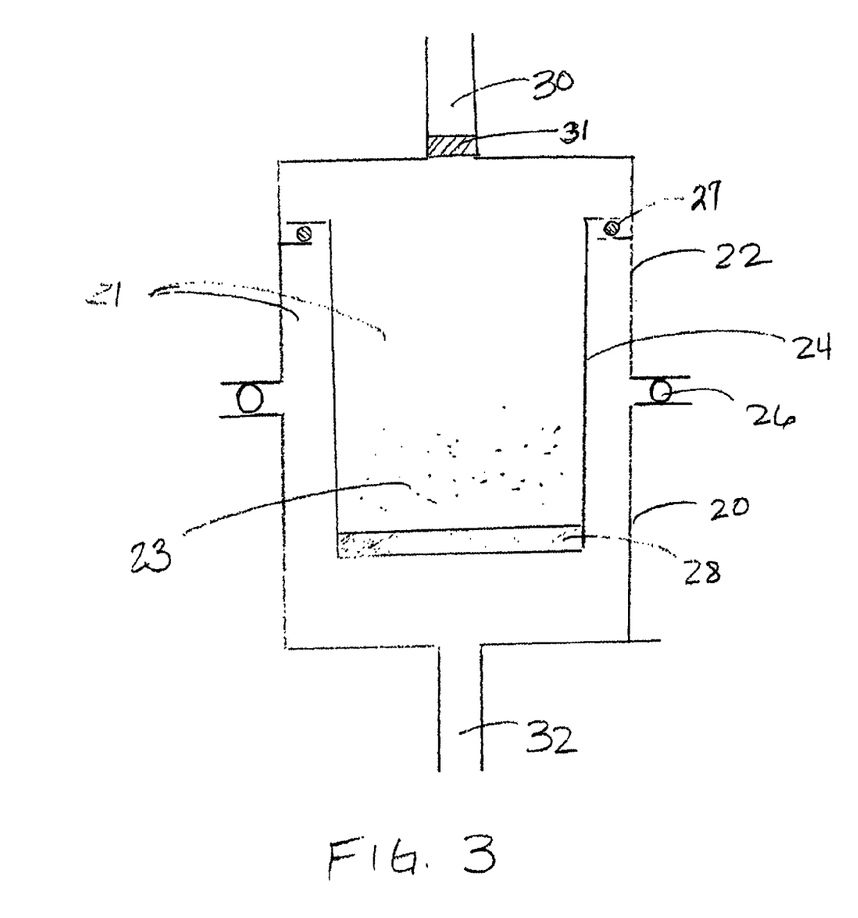
FIG. 3 is a side view of yet a third specific embodiment of a single reactor of the multiple parallel catalytic reactor assembly of the present invention.

Without intending any limitation on the scope of the present invention and as merely illustrative, this invention is explained below in specific terms as applied to specific embodiments of the invention as depicted in the figures. FIGS. 1, 2, and 3 depict only a single reactor for ease of understanding, multiple reactors would be employed in actual practice. Referring now to FIG. 1, bottom 2 is cylindrical in shape and has an open end and a closed end. Vessel 4 has fluid permeable end 6 and is positioned within bottom 2 and contains solid catalyst particles 18. Vessel 4 is supported by supports 5. Top 8 conforms in shape to bottom 2. Frit 19 is attached to top 8. Seal 10, an o-ring, engages both top 8 as well as bottom 2 forming sealed reaction chamber 11. Seal 12, an o-ring, engages top 8 and vessel 4 to direct fluid flow in the proper path. Fluid conduits 14 and 16 are connected to top 8 and are in fluid communication with reaction chamber 11. Reactant is preferably flowed into reaction chamber 11 via fluid conduit 16, the reactant passes through fluid permeable end 6 of vessel 4 and contacts catalyst particles 18. Effluent is withdrawn from reaction chamber 11 via fluid conduit 14.

FIG. 2 is identical to FIG. 1 with the exception that fluid conduit 17 is attached to bottom 2 instead of to top 8 and that an optional thermocouple 16 is shown. Thermocouple 15 extends through top 8 via fluid conduit 14, through frit 19, and into reaction chamber 11.

FIG. 3 shows cylindrical bottom 20 and conforming top 22 with o-ring seal 26 used to engage bottom 20 and top 22 to form reaction chamber 21. Cylindrical vessel 24 is positioned within reaction chamber 21 and has fluid permeable end 28. O-ring seal 27 engages bottom 20 and vessel 24. Vessel 24 contains solid catalyst particles 23 and is contained within reaction chamber 21. Fluid conduit 32 is attached to bottom 20 and is in fluid communication with reaction chamber 21. Fluid conduit 30 is attached to top 22 and is in fluid communication with reaction chamber 21. Frit 31 is attached to fluid conduit 30. Fluid enters reaction chamber 21 via fluid conduit 32 and passes through fluid permeable end 28 of vessel 24 to contact solid catalyst particles 23. Effluent is removed from reaction chamber 21 via fluid conduit 30.

Figure 4:
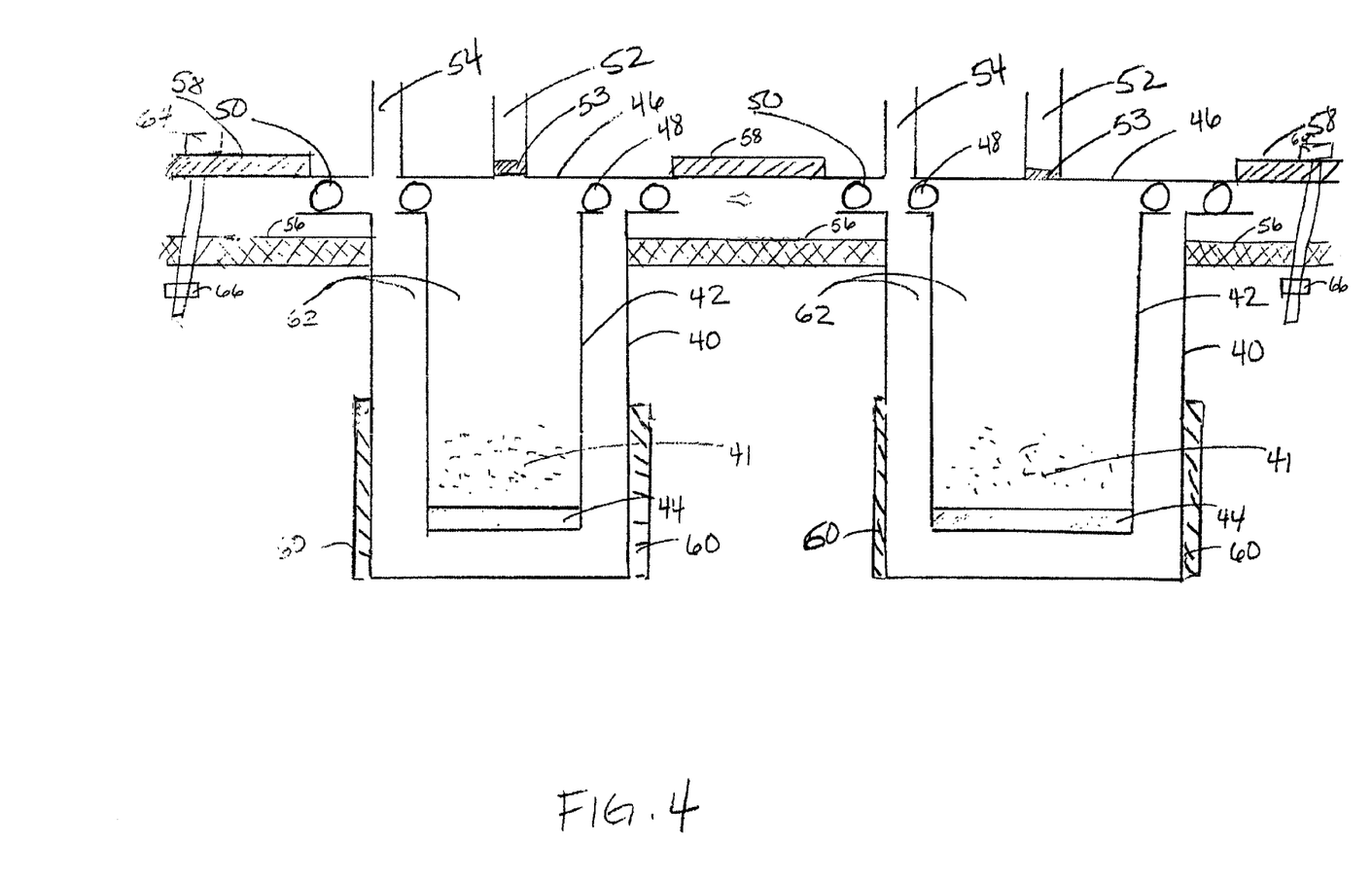
FIG. 4 is a side view of the yet another specific embodiment of the multiple parallel catalytic reactor assembly of the present invention.

FIG. 4 shows a plurality of parallel reactors. Bottoms 40 are cylindrical in shape and each has an open end and a closed end. Vessels 42 have fluid permeable ends 44 and are positioned within bottoms 40 and contain solid catalyst particles 41. Each of the bottoms 40 is attached to support 56. The closed ends of bottoms 40 are in contact with heater 60. Heater 60 is positioned to provide heat to the closed ends of bottoms 40 adjacent to the location of the solid catalyst particles 41 of vessels 42.

Tops 46 conforming in shape to bottoms 40 are attached to top support 58. Seals 50, which are o-rings, engage both the tops 46 as well as the open ends of bottoms 40 forming sealed reaction chambers 62. O-ring seals 48 engage both tops 46 and vessels 42 to seal the proper fluid path. The length of bottoms 40 and vessels 42, the position of heater 60, and the position of seals 50 and 48 are all chosen so that seals 50 and 48 are sufficiently removed from heater 60 so as to be unaffected by the heat of heater 60. Bolts 64 and nuts 66 lock top support 58 and support 66 together. Fluid conduits 62 and 64 are connected to tops 46 and are in fluid communication with reaction chambers 62. Frits 53 are attached to fluid conduits 52.

The multiple parallel catalytic reactor assembly is used to conduct multiple parallel catalytic reactions by first introducing the plurality of catalysts 41 through open ends of the plurality of vessels 42. The plurality of vessels 42 are inserted into the open ends of bottoms 40 so that the open ends of the vessels 42 are aligned with the open ends of bottoms 40. Alternatively, vessels 42 may be first inserted into the open ends of bottoms 40, and then the plurality of catalysts 41 may be introduced through open ends of vessels 42. The plurality of bottoms 40 housing vessels 42 which contain catalysts 41 are simultaneously sealed using the plurality of corresponding tops 46 supported by a single top support 58 to form multiple sealed independent reaction chambers 62. The closed ends of bottoms 40 are heated using heater 60. A reactant fluid is simultaneously introduced via fluid conduits 62 or 64 to each sealed independent reaction chamber to contact the catalysts contained therein and to form a plurality of reaction mixtures, one reaction mixture in each sealed independent reaction chamber 62. Effluent from each independent reaction chamber 62 is simultaneously withdrawn using fluid conduits 54 or 52, whichever was not used to introduce the reactant fluid. The effluent may be analyzed to determine the activity, selectivity and/or yield provided by the catalyst. When the catalysts are spent or the test is complete, the multiple sealed reaction chambers 62 are opened, simultaneously, by removing the plurality of tops 46 from the open ends of the plurality of bottoms 40. The plurality of vessels 42 containing the catalyst particles 41 may then be removed.

It must be emphasized that the above description is merely one embodiment of the present invention and the overall scope of the invention encompasses numerous variations. For example, fluid flow through the reactor may be reversed. In FIG. 1, reactant may be flowed into reaction chamber 11 via fluid conduit 14 passing rough frit 19 to contact catalyst particles 18. Effluent may be withdrawn by passing fluid through fluid permeable end 6 of vessel 4 and through fluid conduit 16; and in FIG. 3 fluid enters reaction chamber 21 via fluid conduit 30 passing through frit 31 to contact solid catalyst particles 23. Effluent is removed through fluid permeable end 28 of vessel 24 and fluid conduit 32. Similarly, it must be emphasized that seals other than o-rings may be employed, and o-rings were shown in the above description merely for ease of understanding.

What is claimed is:

1. A multiple parallel catalytic reactor assembly comprising:
   a) a plurality of bottoms, each bottom having a closed end and an open end, said plurality of bottoms supported by a single first support;
   b) a plurality of tops supported by a single second support, said plurality of tops engaged with said open ends of the plurality of bottoms to form a plurality of independent reaction chambers;
   c) a plurality of vessels, each vessel having a fluid permeable end and an open end, said vessels containing catalyst, said vessels contained within said independent reaction chambers with said open ends of said vessels aligned with said open end of said bottoms;
   d) a plurality of microporous structures in alignment with said open ends of said vessels,
   e) a plurality of first fluid conduits in fluid communication with the plurality of said independent reaction chambers; and
   f) a plurality of second fluid conduits in fluid communication with the plurality of said independent reaction chambers.

2. The multiple parallel catalytic reactor assembly of claim 1 wherein the plurality of microporous structures are attached to said plurality of first or second conduits.

3. The multiple parallel catalytic reactor assembly of claim 1 wherein the plurality of microporous structures are attached to said plurality of vessels.

4. The multiple parallel catalytic reactor assembly of claim 1 wherein the plurality of microporous structures are attached to said plurality of tops.

5. The multiple parallel catalytic reactor assembly of claim 1 wherein the plurality of first conduits are connected to the plurality of tops.

6. The multiple parallel catalytic reactor assembly of claim 1 wherein the plurality of first conduits are connected to the plurality of bottoms.

7. The multiple parallel catalytic reactor assembly of claim 1 wherein the plurality of second conduits are connected to the plurality of tops.

8. The multiple parallel catalytic reactor assembly of claim 1 wherein the plurality of second conduits are connected to the plurality of bottoms.

9. The multiple parallel catalytic reactor assembly of claim 1 wherein the number of parallel reactors in the assembly is at least two and may be increased by adding at least one set of a vessel, a bottom and a corresponding top.

10. The multiple parallel catalytic reactor assembly of claim 1 wherein the number of parallel reactors, n, in the assembly where n is at least 3, may be decreased by removing at least one set of a vessel, a bottom, and a corresponding top.

11. The multiple parallel catalytic reactor assembly of claim 1 further comprising at least one heater adjacent the plurality of bottoms.

12. The multiple parallel catalytic reactor assembly of claim 1 further comprising one or more seals engaging the plurality of bottoms and the plurality of corresponding tops to form the sealed independent reaction chambers.

13. The multiple parallel catalytic reactor assembly of claim 1 further comprising at least one heater adjacent the plurality of bottoms.

14. The multiple parallel catalytic reactor assembly of claim 1 further comprising one or more seals engaging the vessels and corresponding tops.

15. The multiple parallel catalytic reactor assembly of claim 1 further comprising a locking device engaging both the first support and the second support.

16. The multiple parallel catalytic reactor assembly of claim 1 further comprising a plurality of thermocouples extending into the plurality of reaction chambers.

17. The multiple parallel catalytic reactor assembly of claim 1 further comprising at least one support engaging each vessel.

18. A process for conducting multiple parallel catalytic reactions comprising:
   a) containing a plurality of catalysts within a plurality of vessels, each vessel having an open end and a fluid permeable end;
   b) containing the plurality of vessels within a plurality of bottoms, each bottom having a closed end and an open end, said plurality of bottoms supported by a single first support;
   c) sealing, simultaneously, the open ends of the plurality of bottoms with a plurality of corresponding tops supported by a single second support to form multiple sealed independent reaction chambers each multiple sealed independent reaction chamber housing the vessel containing catalyst and further a microporous structure to retain catalyst particles within said sealed independent reaction chambers;
   d) introducing a reactant fluid to each sealed independent reaction chamber to contact the catalysts contained therein and to form a plurality of reaction mixtures, one reaction mixture in each sealed independent reaction chamber; and
   e) withdrawing an effluent devoid of catalyst from each independent reaction chamber.

19. The process of claim 18 further comprising opening, simultaneously, the multiple sealed reaction chambers by removing the plurality of tops from the open ends of the plurality of bottoms.

20. The process of claim 18 further comprising heating at least a portion of at least one of the bottoms in the plurality.

21. The process of claim 18 further comprising removing the plurality of vessels from the plurality of bottoms.

22. The process of claim 18 wherein steps (a) and (b) are performed in any order.

23. The process of claim 18 wherein the introducing of a reactant fluid to each sealed independent reaction chamber of step (d) is performed simultaneously for all sealed independent reaction chambers.

24. The process of claim 18 wherein the withdrawing of an effluent devoid of catalyst from each independent reaction chamber of step (e) is performed simultaneously for all sealed independent reaction chambers.

* * * * *